US005594775A

United States Patent [19]
Hangartner

[11] Patent Number: 5,594,775
[45] Date of Patent: Jan. 14, 1997

[54] METHOD AND APPARATUS FOR THE EVALUATION OF CORTICAL BONE BY COMPUTER TOMOGRAPHY

[75] Inventor: Thomas N. Hangartner, Xenia, Ohio

[73] Assignee: Wright State University, Dayton, Ohio

[21] Appl. No.: 424,841

[22] Filed: Apr. 19, 1995

[51] Int. Cl.$^6$ .................................................. G01D 18/00
[52] U.S. Cl. ............................................ 378/207; 378/54
[58] Field of Search ................................. 378/51, 54, 56, 378/207

[56] References Cited

U.S. PATENT DOCUMENTS 5,247,560  9/1993  Hosokawa et al. .................... 378/54

OTHER PUBLICATIONS

"Constant Cortical Density is a Requirement for the Accurate Measurement of Cortical Thickness by CT" Hangartner et al., Bone and Mineral, Supplement 2 to vol. 25, Apr. 1994, p. S4.

"Measurement of Cortical Bone by Computed Tomography" Hangartner et al., 9th International Bone Bone Densitometry Workshop Abstracts, Sep. 26–30, 1992, p. 30.

*Thickness of the Cortical Layer as an Estimate of Mineral Content of Human Finger Bones*, by P. Virtama, M.D. et al., vol. XXXIII, No. 385, Roentgen Dept. Second Medical Clinic, University Central Hospital, Helsinki, Aug. 1959.

*The Radiological Diagnosis of Osteoporosis: A New Approach*, by Ellis Barnett, D.M.R.D., FFR. et al., Department of Radiology and the University Department of Medicine, Gardiner Institute, Western Infirmary, Glasgow, Apr. 1959.

*Size of Cortical Bone and Relationship to Bone Mineral Density Assessed by Quantitative Computed Tomography Image Segmentation*, Olivia Louis, M.D., Ph.D. et al., Investigative Radiology, vol. 28, No. 9, 802–805, 1993.

*Primary Examiner*—Don Wong
*Attorney, Agent, or Firm*—Killworth, Gottman, Hagan & Schaeff

[57]  ABSTRACT

This invention includes a computed tomography (CT) system which has the ability to quantitate cortical bone. Based on a series of specialized phantom measurements, the characteristics of the CT scanner with respect to the evaluation of cortical bone are established. The resulting characteristics provide the input to a specific algorithm that analyzes cross-sectional images containing cortical bone.

14 Claims, 7 Drawing Sheets

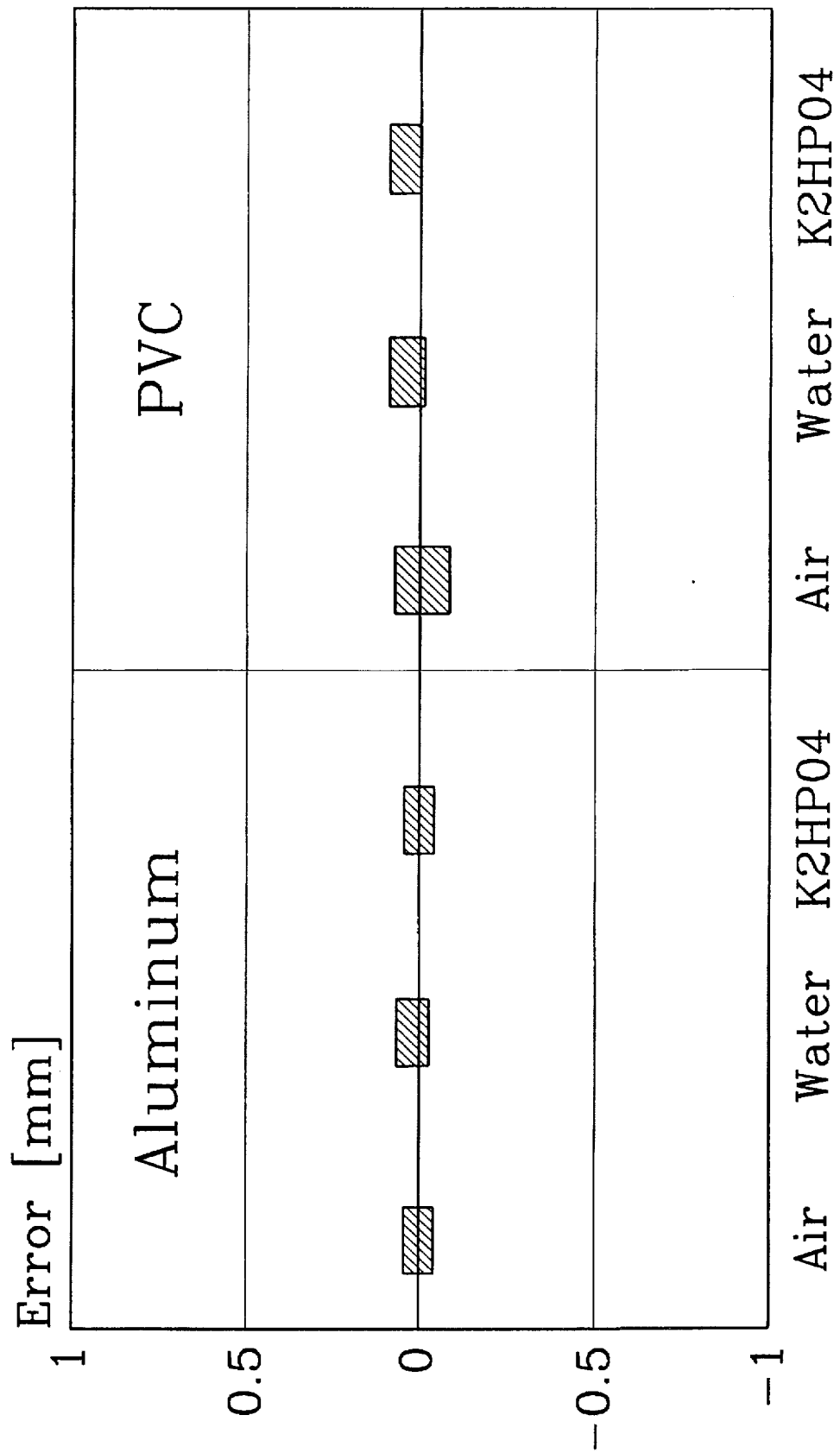

5,594,775

METHOD AND APPARATUS FOR THE EVALUATION OF CORTICAL BONE BY COMPUTER TOMOGRAPHY

FIELD OF THE INVENTION

The present invention relates to computed tomography and in particular to the measurement of cortical bone with computed tomography.

BACKGROUND OF THE INVENTION

The major obstacles involved in the calculation of both width and density for cortical bone are based on the insufficient resolution of the CT scanners relative to the size of the structures of interest. This insufficient resolution leads to the partial volume effect, a blurring of the edges and misrepresentation of the true density of the bone.

SUMMARY OF THE INVENTION

A specialized phantom allows characterization of the scanner's resolution with respect to structures of various sizes and densities. These results are then used as calibration input to an algorithm which in turn extracts and analyzes the structures of interest from CT images.

BRIEF DESCRIPTION OF THE DRAWINGS

FIG. 7 graphically represents the accuracy of the width measurements based on the method shown in FIG. 6.

DETAILED DESCRIPTION OF THE PREFERRED EMBODIMENT INDUSTRIAL CONTROLLER HARDWARE

Industrial Controller Hardware

Measurement Procedures

To show the universal nature of the invention, all CT measurements were performed on two different scanners: GE-9800 (General Electric, Milwaukee, Wis.) and Osteo-Quant® (in-house built system). For the GE-9800, the standard bone-measurement protocol was used. The liquid Cann-Genant calibration standard was employed for the phantom measurements and the solid GE calibration standard for the femur measurements. The bone reconstruction option provides steeper edges between soft tissue and bone. This option was, therefore, used for all reconstructions. For the evaluations, the images were transferred to a VAX 8350 laboratory computer, where all analysis was performed with custom software.

The measurements performed on the OsteoQuant® were executed with the normal clinical program. The Osteo-Quant® is a specially built CT scanner, optimized for the highly precise measurement of trabecular bone in arms and legs. The scanner contains 16 beams, generated by an $I^{125}$ source and arranged in a second-generation translate-rotate geometry. One measurement Hakes 90 seconds and provides an image with 256×256 pixels. The pixel size is 0.3 mm for a forearm measurement; 0.6 mm holes arranged at 0.6 mm intervals can be resolved. The scans on the OsteoQuant® do not require a concurrently measured calibration phantom because of the extremely good short- and long-term stability of the scanner.

Phantom Evaluations

Figure 1:
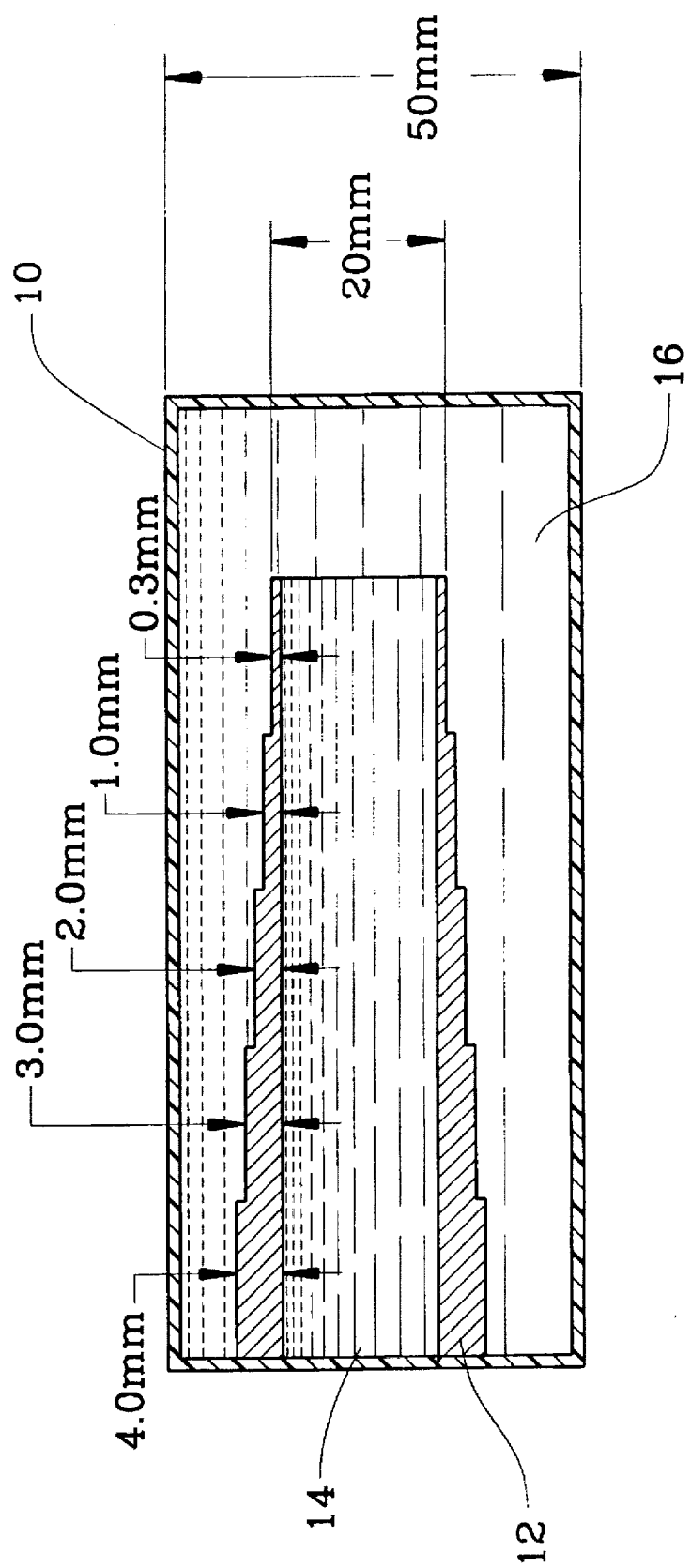
FIG. 1 is a cross-sectional view of a cylindrical phantom having a stepped outer surface to provide five separate simulated cortical widths from 0.3 mm to 4.0 mm and for use with the present invention.
Figure 2:
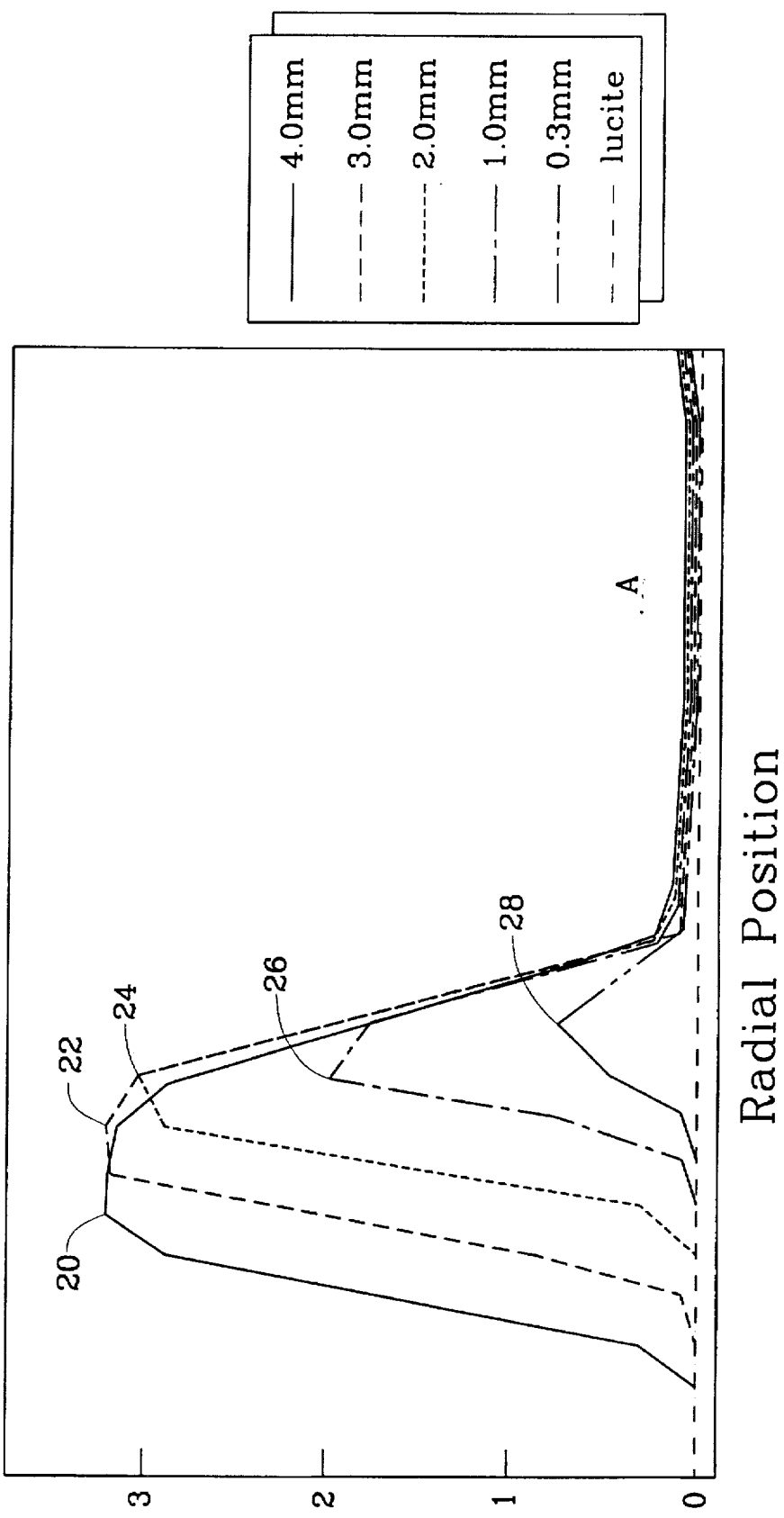
FIG. 2 is a plot of total image density for tomographic images of the phantom of FIG. 1, taken in a plane perpendicular to the axis of the cylinder of the phantom, within a circular region of interest, as a function of the radius of the region of interest.

In order to simulate various cortical thicknesses, a phantom was constructed that consisted of an outer cylinder of lucite 10 with an inner stepped cylindrical insert 12 of aluminum, PVC, or some other test material (FIG. 1). The insert is filled with a solution 14 of 150 mg/ml $K_2HPO_4$ to mimic trabecular bone. Alternatively, measurements may be performed with water or air in the center of the insert 12. The space 16 between the insert 12 and the lucite container 10 is filled with water to mimic soft tissue. For the measurements on the OsteoQuant®, this phantom was scanned by itself; for the measurements on the GE-9800 scanner, the phantom was inserted into a whole-body water phantom. After obtaining scans at each cortical thickness, the images were subjected to an algorithm that identified the exact center of the cortical insert. A circular region of interest, with the approximate size of the outer cortical boundary, was moved in small increments until the sum of all pixels within this region showed a maximum. The average pixel values within concentric shells provided a smooth radial profile of the density distribution across the cortex. The smooth radial profiles of aluminum cylinders in water are illustrated in FIG. 2. All subsequent evaluations were based on these profiles.

The profiles, as shown in FIG. 2, illustrate some of the basic problems concerning the evaluation of the cortex. As long as the cortical structure is large enough, the peak value representing the cortical density is reached. The transition from the cortex to the adjacent tissue requires several pixels, although the phantom contains these materials side by side. The values, indicated generally at A in FIG. 2, representing the center of the insert are systematically higher for profiles with larger cortical thicknesses. This issue is related to scatter.

Figure 3:
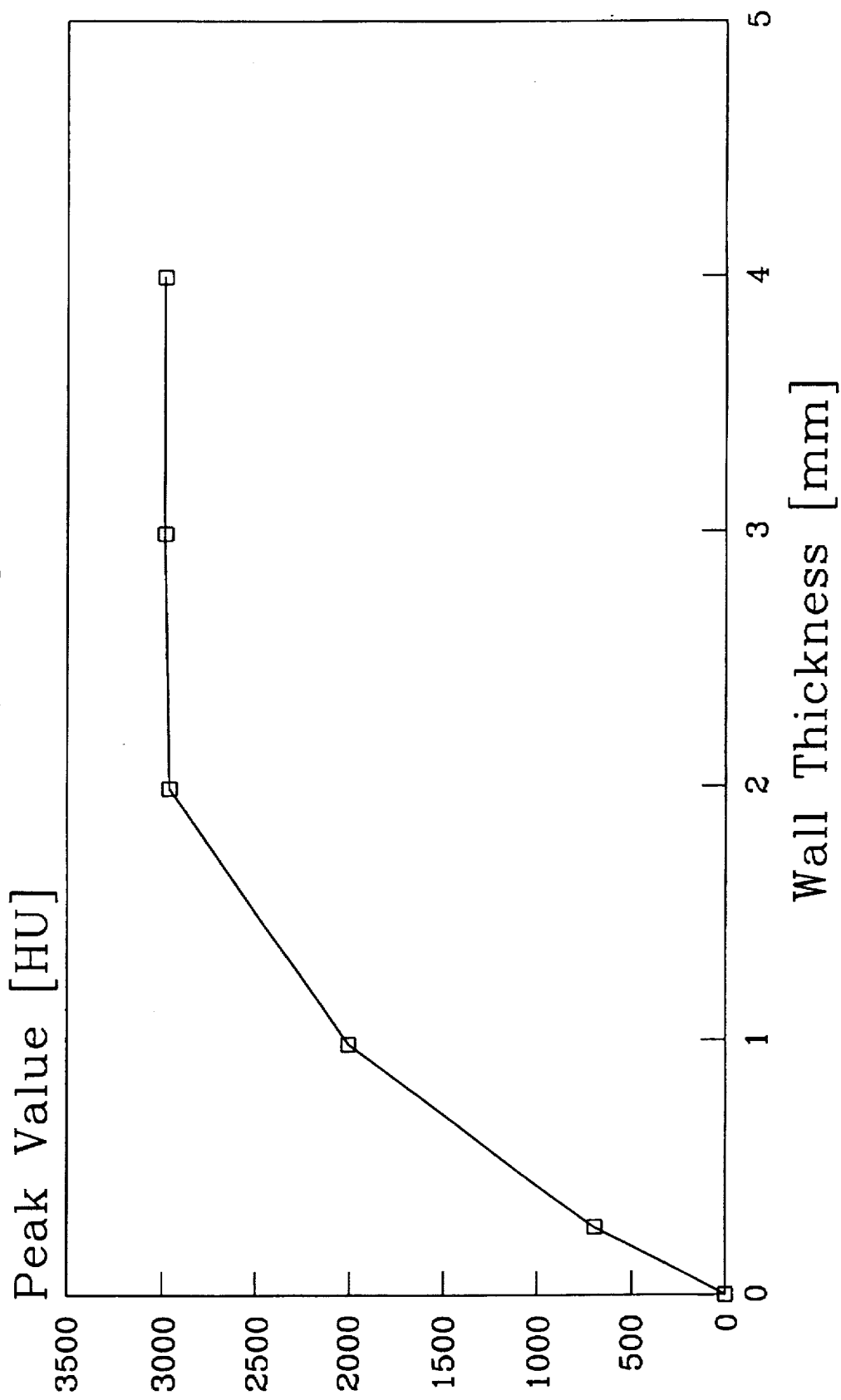
FIG. 3 is a plot showing the peak densities of FIG. 2 corresponding to the different simulated cortical widths of the phantom of FIG. 1.

FIG. 3 illustrates imaged cortical density as a function of structure thickness for a wall material of aluminum. The measurement was performed on the GE-9800. The representation of peak cortical value versus cortical thickness, illustrated in FIG. 3, shows the minimum size for the cortex necessary for accurate density evaluations. The minimal thickness of the cortex must be about 2.5 mm for the GE-9800 and 2.0 mm for the OsteoQuant®. The slight decline of the OsteoQuant® peak values for the 3 and 4 mm thick cortices is likely based on an under corrected beam-hardening effect.

Figure 4:
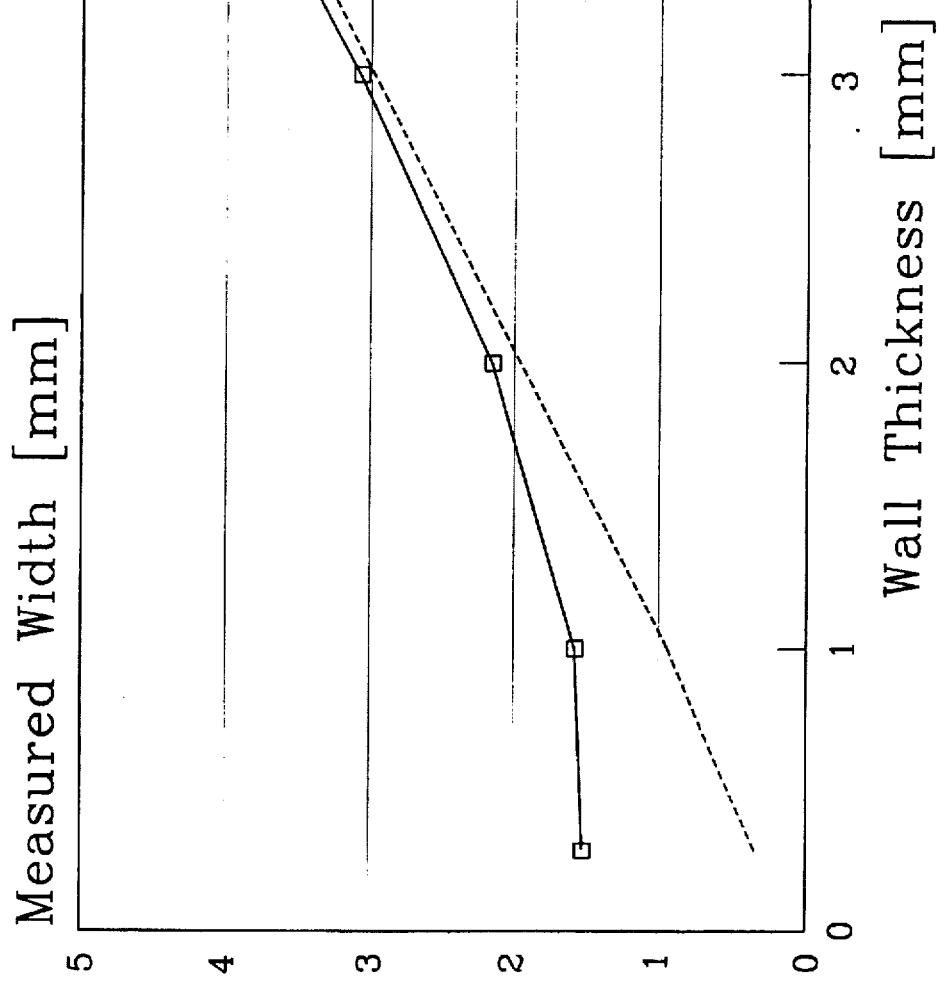
FIG. 4 is a plot of measured width vs. actual width of the simulated cortical bone of the phantom of FIG. 1 for a conventional method (FWHM) of measuring width.

As noted above, FIG. 2 illustrates the density profiles. Each curve has a maximum density value and a corresponding half maximum value. Further, each curve has a width along the radial position axis (mm) corresponding to the half maximum value. A conventional attempt at analyzing the cortical thickness consists of measuring the width of the profile at FWHM (full width at half maximum). FIG. 4 illustrates the results of evaluation of cortical wall thickness based on the FWHM method. For those cortical thicknesses where the profiles reach the correct peak value, the width measurements follow the slope of the identity line. Towards smaller cortical thicknesses, the widths are more and more overestimated.

Figure 5:
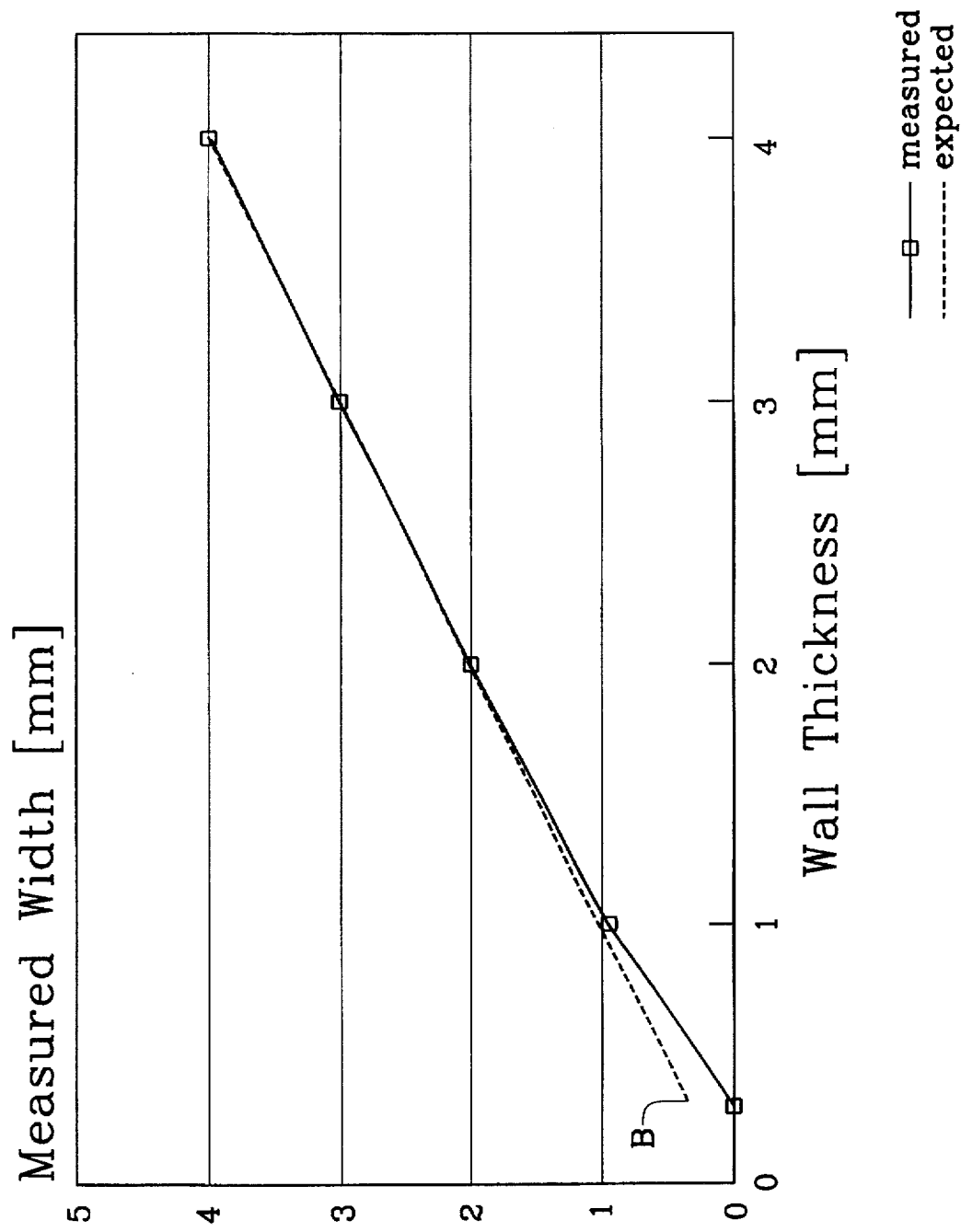
FIG. 5 is a plot of measured width vs. actual width of the simulated cortical bone of the phantom of FIG. 1 for a method (optimized fixed threshold) of measuring width according to the present invention.

An alternative to the FWHM measurement is a thickness measurement according to the present invention, wherein cortical wall thickness is evaluated based on an optimized fixed threshold. A common threshold was used for all profiles. This threshold was optimized to provide the smallest overall error in width measurements. Table 1 demonstrates examples of optimal thresholds found using phantoms having known wall widths. The phantoms allow characterization of the scanner's resolution with respect to structures of various sizes and densities. The threshold was only optimized for the profiles whose peak crossed the threshold. FIG. 2 shows profiles having peaks indicated generally at 20, 22, 24, 26 and 28. Peaks 20, 22, 24 and 26 would cross a line corresponding to a threshold density value slightly less than 2000 HU (Hounsfield Unit). FIG. 5 illustrates evaluation of cortical wall thickness based on an optimized fixed threshold. The cortical thickness of 0.3 mm, indicated at B, could not be evaluated on any of the two scanners.

Comparison of all combinations of phantom measurements, with PVC or aluminum as the insert and 150 mg/ml $K_2HPO_4$, water or air in the center, revealed that the optimal threshold is a certain fixed percentage of the difference between the two adjacent materials. This percentage threshold appeared to be strongly dependent on the material representing the cortex, at least for the OsteoQuant®. Table 1 demonstrates optimal thresholds for thickness measurements with the GE-9800 and the OsteoQuant.

TABLE 1

| Phantom | GE-9800 | OsteoQuant ® |
|---|---|---|
| Aluminum | 52% | 30% |
| PVC | 51% | 45% |

Figure 6:
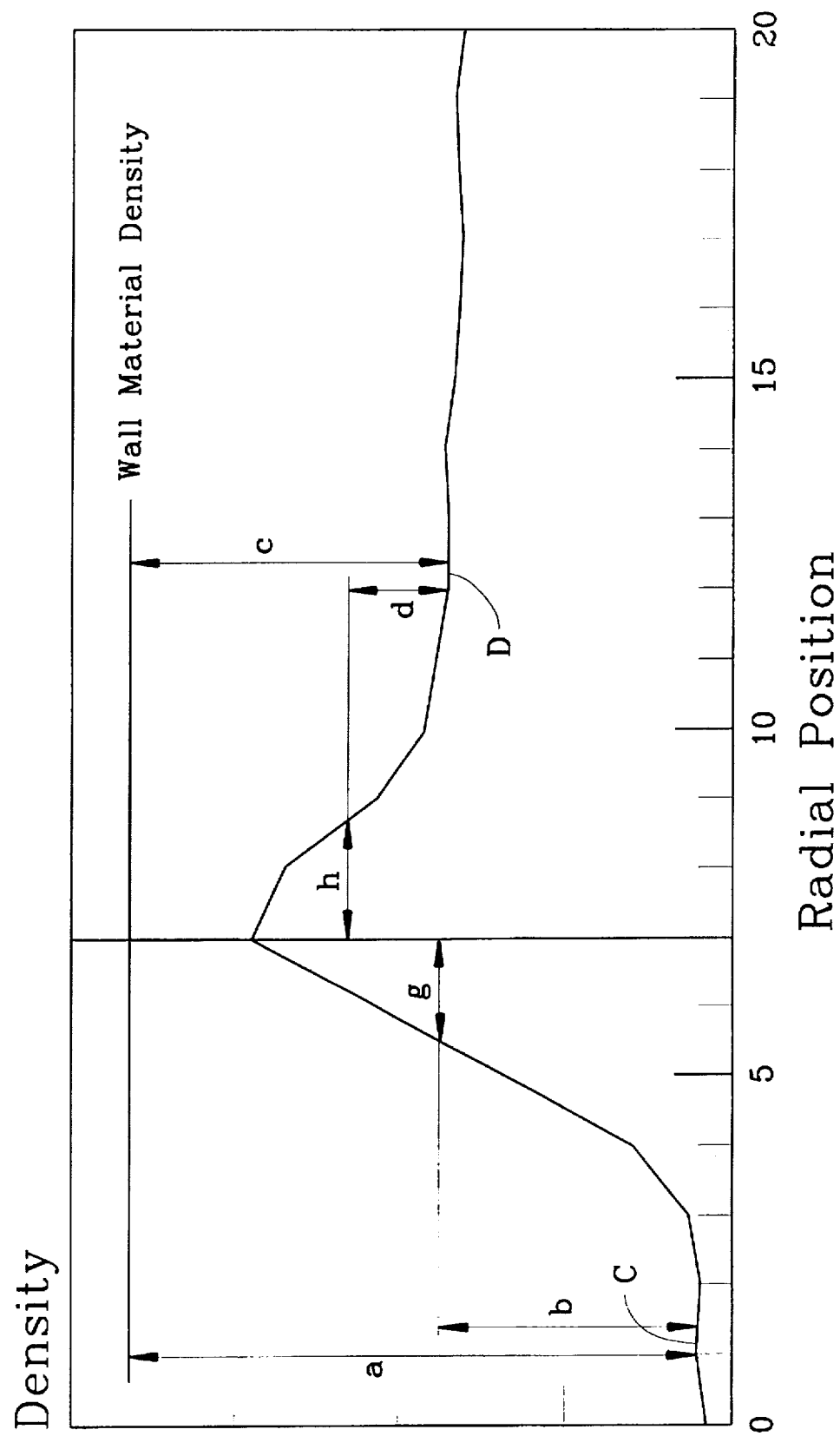
FIG. 6 is a plot similar to that of FIG. 2 showing a method of measuring cortical width according to the present invention.

FIG. 6 illustrates the method of evaluating the wall thickness of a structure according to the preferred embodiment. Different materials are located adjacent to the outer and inner boundary of the wall and are indicated by the first series of substantially constant density values outside and inside the wall at C and D. According to the present invention, cortical width is obtained by combining two half-widths, g and h, each based on a different threshold b, d. Each threshold, b and d, however, is calculated from the constant percentage threshold t. As noted above, an optimal threshold t provides the smallest overall error in width measurements for the profiles whose peak crosses the threshold. Table 1 demonstrates examples of optimal thresholds found using phantoms having known wall widths for two different instruments.

As illustrated in FIG. 6, the threshold density value is influenced by the different materials adjacent to the cortex periosteally and endosteally. The threshold b is calculated by multiplying the percentage threshold t by the difference between the wall material density and the density of the material adjacent to the outer boundary of the wall ($b=t \times a$).

Threshold d is calculated by multiplying the percentage threshold t by the difference between the wall material density and the density of the material adjacent to the inner boundary of the wall ($d=t \times c$). The half width g is measured at a point on the profile having a density value equal to the threshold value b added to a density value of a substantially constant portion of the density profile outside of the wall. The half width h is measured at a point on the profile having a density value equal to the threshold value d added to a density value of a substantially constant portion of the density profile inside of the wall. The two half widths, g and h, are combined to determine cortical width ($w=g+h$).

The range of errors observed in the cortical width measurements for all combinations of phantom materials is shown in FIG. 7. It appears that cortical thickness can be measured on a GE-9800 with a maximum error of ±0.10 mm, on the OsteoQuant® with ±0.2 mm. Due to interpolation between profile values, these errors are smaller than the size of a pixel.

As stated before, the correct cortical density value is reached only if the structure has a certain minimal width. It is possible, however, to calculate the correct density of the structure even if this minimal width is not reached. Based on the partial volume effect, the imaged density is systematically reduced with decreasing width of the structure (FIG. 3). After calculation of the correct width as outlined above, a calibration curve of density versus width provides a correct reading of the density.

Although bone is the major tissue of interest with respect to this invention, any other tissue that shows with a minimal amount of contrast relative to the surrounding tissue can be analyzed this way.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made:

I claim:

1. A method of measuring the width of a structure comprising the steps of:

obtaining x-ray image data of a structure with a computed tomography scanner;

determining a profile of density across the structure from the x-ray image data;

measuring a first half-width of the profile corresponding to a first density value, wherein said first density value is a function of a first threshold value;

measuring a second half-width of the profile corresponding to a second density value, wherein said second density value is a function of a second threshold value;

determining the width of the structure by adding the first half-width to the second half-width.

2. A method of measuring the width of a structure as claimed in claim 1 wherein said first density value is lower than said second density value.

3. A method of measuring the width of a structure as claimed in claim 1 wherein said first threshold value is calculated by multiplying a first density difference by an optimized percentage threshold, and wherein said second threshold value is calculated by multiplying a second density difference by said optimized percentage threshold.

4. A method of measuring the width of a structure as claimed in claim 3 wherein said first density difference is a difference between a density of the structure and a density of a first adjacent material, and said second density difference is a difference between the density of the structure and a density of a second adjacent material.

5. A method of measuring the width of a structure as claimed in claim 4 wherein the density of the first adjacent material corresponds to a substantially constant density portion of the density profile preceding the structure, and wherein the density of the second adjacent material corresponds to a substantially constant density portion of the density profile following the structure.

6. A method of measuring the width of a structure as claimed in claim 4 wherein said first density value is the sum of said first threshold value and the density of said first adjacent material, and wherein said second density value is the sum of said second threshold value and the density of said second adjacent material.

7. A method of measuring the width of a structure as claimed in claim 3 wherein said optimized percentage threshold is determined by selecting a percentage threshold which provides the smallest overall error in width measurements using a phantom having known widths.

8. A method of measuring the cortical width of a bone comprising the steps of:
- obtaining x-ray image data of a bone with a computed tomography scanner;
- determining a profile of density across the cortex of the bone from the x-ray image data;
- measuring a first half-width of the profile corresponding to a first density value, wherein said first density value is a function of a first threshold value;
- measuring a second half-width of the profile corresponding to a second density value, wherein said second density value is a function of a second threshold value;
- determining the width of the cortex by adding the first half-width to the second half-width.

9. A method of measuring the cortical width of a bone as claimed in claim 8 wherein said first density value is lower than said second density value.

10. A method of measuring the cortical width of a bone as claimed in claim 8 wherein said first threshold value is calculated by multiplying a first density difference by an optimized percentage threshold, and wherein said second threshold value is calculated by multiplying a second density difference by said optimized percentage threshold.

11. A method of measuring the cortical width of a bone as claimed in claim 10 wherein said first density difference is a difference between a density of the bone and a density of a first adjacent material, and said second density difference is a difference between the density of the bone and a density of a second adjacent material.

12. A method of measuring the cortical width of a bone as claimed in claim 11 wherein the density of the first adjacent material corresponds to a substantially constant density portion of the density profile preceding the bone, and the density of the second adjacent material corresponds to a substantially constant density portion of the density profile following the bone.

13. A method of measuring the cortical width of a bone as claimed in claim 11 wherein said first density value is the sum of said first threshold value and the density of said first adjacent material, and wherein said second density value is the sum of said second threshold value and the density of said second adjacent material.

14. A method of measuring the cortical width of a bone as claimed in claim 10 wherein said optimized percentage threshold is determined by selecting a percentage threshold which provides the smallest overall error in width measurements using a phantom having known widths.

* * * * *